(12) United States Patent
Kubo

(10) Patent No.: US 11,311,185 B2
(45) Date of Patent: Apr. 26, 2022

(54) ENDOSCOPE SYSTEM

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 187 days.

(21) Appl. No.: 16/788,945

(22) Filed: Feb. 12, 2020

(65) Prior Publication Data

US 2020/0260941 A1 Aug. 20, 2020

(30) Foreign Application Priority Data

Feb. 19, 2019 (JP) .............................. JP2019-027188

(51) Int. Cl.
*A61B 1/06* (2006.01)
*A61B 1/00* (2006.01)
*G06T 7/00* (2017.01)

(52) U.S. Cl.
CPC .......... *A61B 1/0638* (2013.01); *A61B 1/0005* (2013.01); *A61B 1/00009* (2013.01); *A61B 1/0676* (2013.01); *G06T 7/0012* (2013.01); *G06T 2207/10068* (2013.01)

(58) Field of Classification Search
CPC .................................................. A61B 1/0638
See application file for complete search history.

(56) References Cited

U.S. PATENT DOCUMENTS

| | | |
|---|---|---|
| 2006/0209185 A1 | 9/2006 | Yokoi |
| 2014/0316279 A1 | 10/2014 | Morishita |
| 2015/0009310 A1* | 1/2015 | Morimoto ................ A61B 1/05 348/68 |
| 2015/0094538 A1 | 4/2015 | Terakawa |
| 2016/0262602 A1* | 9/2016 | Yu ........................ A61B 1/0638 |
| 2017/0014022 A1 | 1/2017 | Tamura et al. |

FOREIGN PATENT DOCUMENTS

| | | |
|---|---|---|
| JP | 2005-143991 A | 6/2005 |
| JP | 2009-039510 A | 2/2009 |
| JP | 2013-183911 A | 9/2013 |
| JP | 2015-066050 A | 4/2015 |

(Continued)

OTHER PUBLICATIONS

An Office Action; "Notice of Reasons for Refusal," mailed by the Japanese Patent Office dated Nov. 30, 2021, which corresponds to Japanese Patent Application No. 2019-027188 and is related to U.S. Appl. No. 16/788,945 with English translation.

(Continued)

*Primary Examiner* — Daniel T Tekle
(74) *Attorney, Agent, or Firm* — Studebaker & Brackett PC

(57) ABSTRACT

First illumination light having a first peak wavelength range and second illumination light having a second peak wavelength range different from the first peak wavelength range are automatically switched and emitted. Identification processing for allowing a first object to be observed and a second object to be observed to be identified in a composite display image is performed. The first object to be observed has a first absorption peak in the first peak wavelength range of the first illumination light and the second object to be observed has a second absorption peak in the second peak wavelength range of the second illumination light.

12 Claims, 12 Drawing Sheets

(56) References Cited

FOREIGN PATENT DOCUMENTS

| | | |
|---|---|---|
| JP | 2015-196004 A | 11/2015 |
| WO | 2013115323 A1 | 8/2013 |
| WO | 2016151676 A1 | 9/2016 |

OTHER PUBLICATIONS

An Office Action; "Notice of Reasons for Refusal", mailed by the Japanese Patent Office dated Mar. 8, 2022, which corresponds to Japanese Patent Application No. 2019-027188 and is related to U.S. Appl. No. 16/788,945; with English language translation.

* cited by examiner

ENDOSCOPE SYSTEM

CROSS-REFERENCE TO RELATED APPLICATIONS

This application claims priority under 35 U.S.C § 119(a) to Japanese Patent Application No. 2019-027188 filed on Feb. 19, 2019. The above application is hereby expressly incorporated by reference, in its entirety, into the present application.

BACKGROUND OF THE INVENTION

1. Field of the Invention

The present invention relates to an endoscope system that switches and displays plural kinds of images.

2. Description of the Related Art

In recent years, an endoscope system comprising a light source device, an endoscope, and a processor device has been widely used in a medical field. In the endoscope system, illumination light is applied to an object to be observed from the endoscope, and the image of the object to be observed is displayed on a monitor on the basis of RGB image signals that are obtained in a case where the image of the object to be observed, which is being illuminated with the illumination light, is picked by an image pickup sensor of the endoscope.

An object to be observed includes bile, such as bilirubin, fat, such as a carcinoid, and the like in addition to blood contained in a blood vessel, and the like. However, the spectral absorption peaks of blood, bile, and fat are close to each other in a blue-light wavelength range. For this reason, in a case where the image of an object to be observed including blood, bile, fat, and the like is picked up by an RGB color image pickup sensor, all components related to blood, bile, and fat are included in B-pixels of the image pickup sensor. Accordingly, it is difficult to distinguish blood, bile, and fat and to exclusively emphasize blood, bile, and fat. In contrast, WO2013/115323A (corresponding to US2014/316279A1) discloses a technique that picks up the image of fat using the spectrum of light reflected from fat by spectroscopic means or the like to observe fat and the like. Further, WO2016/151676A discloses a technique that separates blood and fat using image processing.

SUMMARY OF THE INVENTION

In a case where blood, bile, and fat are to be observed as described above, a plurality of pieces of illumination light having peak wavelengths corresponding to the spectral absorption peaks of blood, bile, and fat are switched and an object to be observed is illuminated with the pieces of illumination light so that blood, bile, and fat can be distinguished. Further, there is a request for a method of displaying blood, bile, and fat to allow blood, bile, and fat to be identified on a monitor on the basis of images that are obtained under the switching illumination using the plurality of pieces of illumination light.

An object of the invention is to provide an endoscope system that can display a plurality of objects to be observed of which spectral absorption peaks are close to each other, such as blood, bile, and fat, to allow the objects to be observed to be identified.

An endoscope system according to an aspect of the invention comprises a light source unit that emits first illumination light having a first peak wavelength range and second illumination light having a second peak wavelength range different from the first peak wavelength range, a light source control unit that automatically switches and emits the first illumination light and the second illumination light for a light emission period of at least one or more frames, a color image pickup sensor that includes specific pixels provided with specific color filters transmitting light having a wavelength range corresponding to the first peak wavelength range and light having a wavelength range corresponding to the second peak wavelength range, an image acquisition unit that acquires first image signals obtained in a case where an image of an object to be observed illuminated with the first illumination light is picked up by the image pickup sensor and second image signals obtained in a case where an image of an object to be observed illuminated with the second illumination light is picked up by the image pickup sensor, and a composite display image-processing unit that performs identification processing for allowing a first object to be observed and a second object to be observed to be identified in a composite display image in a case where the composite display image-processing unit synthesizes the first image signals and the second image signals to generate the composite display image. The first object to be observed has a first absorption peak in the first peak wavelength range of the first illumination light, and the second object to be observed has a second absorption peak in the second peak wavelength range of the second illumination light.

It is preferable that a component related to the first absorption peak of the first object to be observed is included in a specific color signal of the first image signal, a component related to the second absorption peak of the second object to be observed is included in a specific color signal of the second image signal, and the identification processing includes first identification processing for comparing a signal value of the specific color signal of the first image signal with a signal value of the specific color signal of the second image signal by comparison processing and displaying the first object to be observed and the second object to be observed to allow the first object to be observed and the second object to be observed to be identified in the composite display image by using a result of the comparison processing. It is preferable that the specific color signal of the first image signal is displayed in the composite display image in the first identification processing. It is preferable that the specific color signal of the second image signal is displayed in the composite display image in the first identification processing. It is preferable that a signal having a smaller signal value between the specific color signal of the first image signal and the specific color signal of the second image signal is displayed in the composite display image and a signal having a larger signal value therebetween is not displayed in the composite display image in the first identification processing. It is preferable that a signal having a larger signal value between the specific color signal of the first image signal and the specific color signal of the second image signal is displayed in the composite display image and a signal having a smaller signal value therebetween is not displayed in the composite display image in the first identification processing.

It is preferable that a component related to the first absorption peak of the first object to be observed is included in a specific color signal of the first image signal, a component related to the second absorption peak of the second object to be observed is included in a specific color signal of the second image signal, and the identification processing includes second identification processing for performing arithmetic processing for identification based on the specific color signal of the first image signal and the specific color signal of the second image signal and displaying the first object to be observed and the second object to be observed to allow the first object to be observed and the second object to be observed to be identified in the composite display image by using a result of the arithmetic processing for identification. It is preferable that an arithmetic value obtained by subtracting an absolute value of a difference value between the signal value of the specific color signal of the first image signal and the signal value of the specific color signal of the second image signal from an average value of the signal value of the specific color signal of the first image signal and the signal value of the specific color signal of the second image signal is obtained and the composite display image is displayed using the arithmetic value in the second identification processing.

It is preferable that the specific pixel is a B-pixel provided with a B-filter as the specific color filter. It is preferable that the first peak wavelength range is in a range of 400 nm to 430 nm and the second peak wavelength range is in a range of 430 nm to 500 nm. It is preferable that the first absorption peak is included in a wavelength range including a wavelength of 410 nm and the second absorption peak is included in a wavelength range including a wavelength of 440 nm or 450 nm. It is preferable that the first object to be observed is blood and the second object to be observed is bile or fat.

An endoscope system according to another aspect of the invention comprises a light source unit that emits first illumination light having a first peak wavelength range and second illumination light having a second peak wavelength range different from the first peak wavelength range, a light source control unit that automatically switches and emits the first illumination light and the second illumination light for a light emission period of at least one or more frames, a color image pickup sensor that includes specific pixels provided with specific color filters transmitting light having a wavelength range corresponding to the first peak wavelength range and light having a wavelength range corresponding to the second peak wavelength range, an image acquisition unit that acquires first image signals obtained in a case where an image of an object to be observed illuminated with the first illumination light is picked up by the image pickup sensor and second image signals obtained in a case where an image of an object to be observed illuminated with the second illumination light is picked up by the image pickup sensor, and a display control unit that alternately displays a first display image based on the first image signals and a second display image based on the second image signals at regular intervals by a display unit to display the first object to be observed and the second object to be observed by the display unit and to allow a first object to be observed and a second object to be observed to be identified. The first object to be observed has a first absorption peak in the first peak wavelength range of the first illumination light, and the second object to be observed has a second absorption peak in the second peak wavelength range of the second illumination light.

According to the invention, it is possible to display a plurality of objects to be observed of which spectral absorption peaks are close to each other, such as blood, bile, and fat, to allow the objects to be observed to be identified.

DESCRIPTION OF THE PREFERRED EMBODIMENTS

First Embodiment

Figure 1:
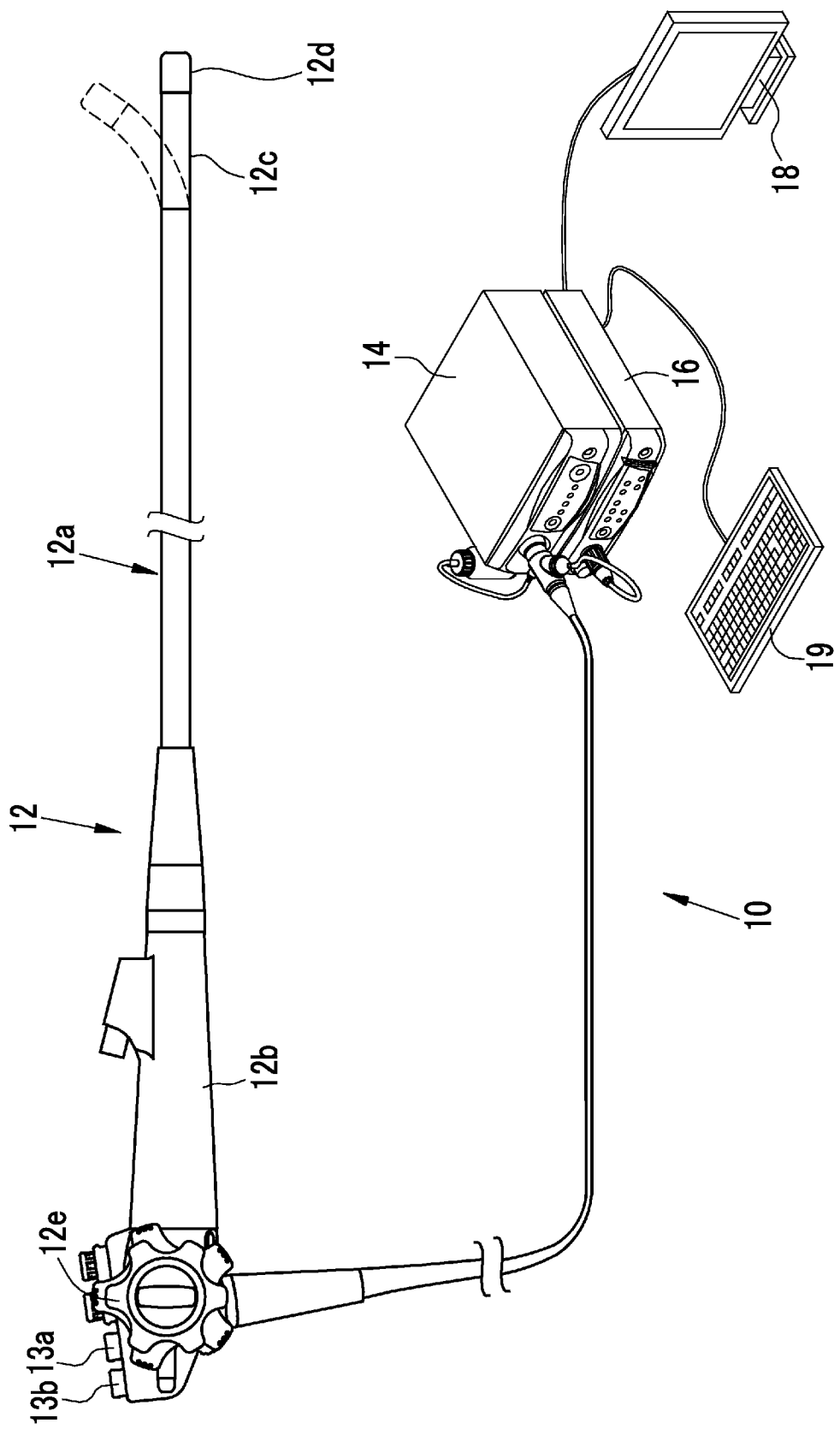
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18 (display unit), and a user interface 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d faces in a desired direction. The user interface 19 includes a mouse and the like in addition to a keyboard shown in FIG. 1.

Further, the operation part 12b is provided with a mode changeover switch 13a and a static image-acquisition instruction unit 13b in addition to the angle knobs 12e. The mode changeover switch (SW) 13a is used for an operation for switching a normal light observation mode and a composite display mode. The normal light observation mode is a mode where a normal image is displayed on the monitor 18. The composite display mode is a mode where a composite display image is displayed on the monitor 18. A first object to be observed (for example, blood) and a second object to be observed (for example, bile or fat) of which the absorption characteristics of light are similar to each other in a blue-light wavelength range are displayed in the composite display image to be identifiable. A foot switch may be used as a mode switching unit, which is used to switch a mode, other than the mode changeover switch 13a.

The processor device 16 is electrically connected to the monitor 18 and the user interface 19. The monitor 18 outputs and displays image information and the like. The user interface 19 functions as a user interface (UI) that receives an input operation, such as function settings. An external recording unit (not shown), which records image information and the like, may be connected to the processor device 16.

Figure 2:
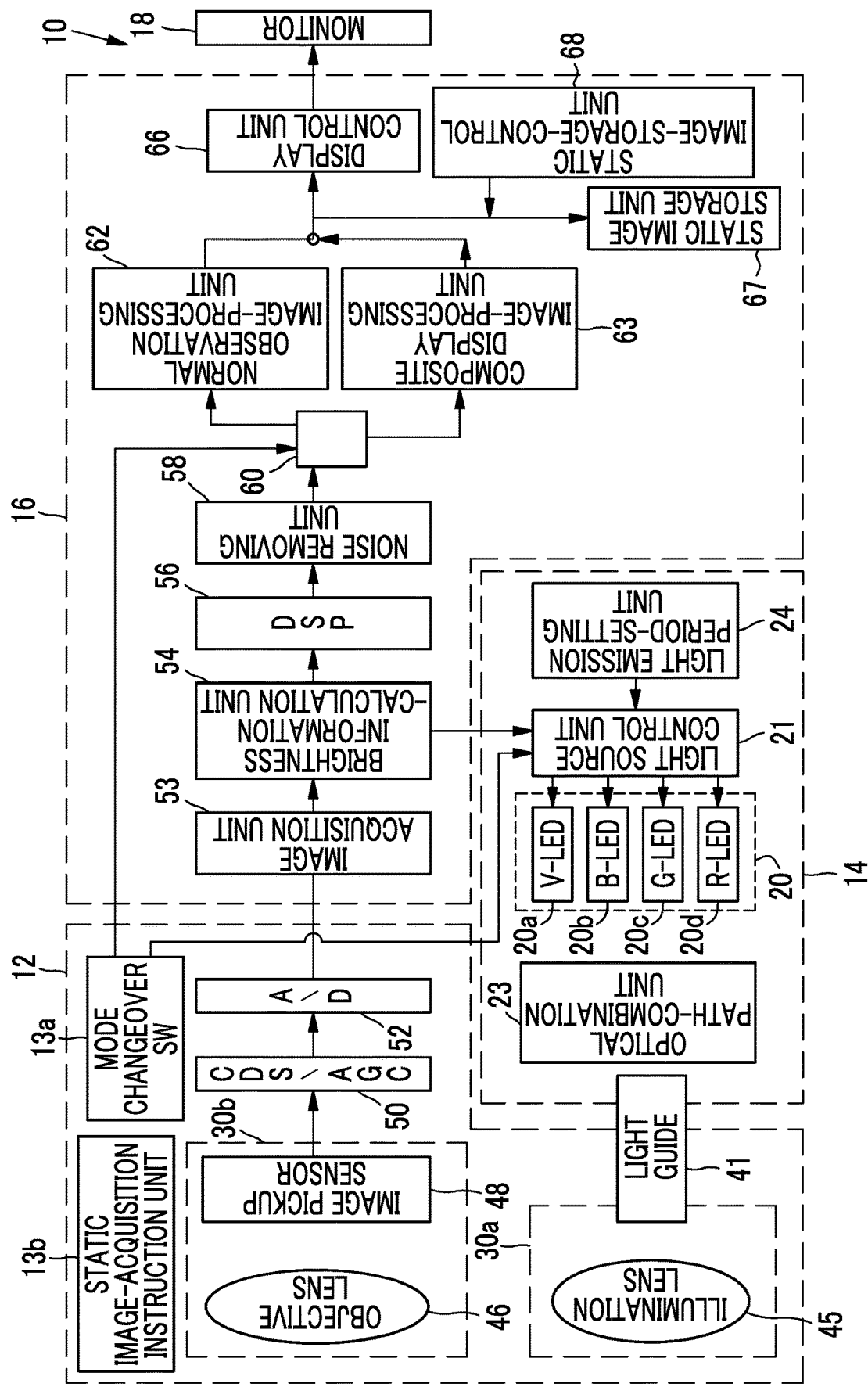
FIG. 2 is a block diagram showing the functions of the endoscope system according to the first embodiment.

As shown in FIG. 2, the light source device 14 includes a light source unit 20, a light source control unit 21, and an optical path-combination unit 23. The light source unit 20 includes a violet light emitting diode (V-LED) 20a, a blue light emitting diode (B-LED) 20b, a green light emitting diode (G-LED) 20c, and a red light emitting diode (R-LED) 20d. The light source control unit 21 controls the drive of the LEDs 20a to 20d. The optical path-combination unit 23 combines the optical paths of pieces of light that are emitted from the four color LEDs 20a to 20d and have four colors. The pieces of light, which are combined by the optical path-combination unit 23, are applied to the inside of an object to be examined through a light guide 41 and an illumination lens 45 that are inserted into the insertion part 12a. A laser diode (LD) may be used instead of the LED.

Figure 3:
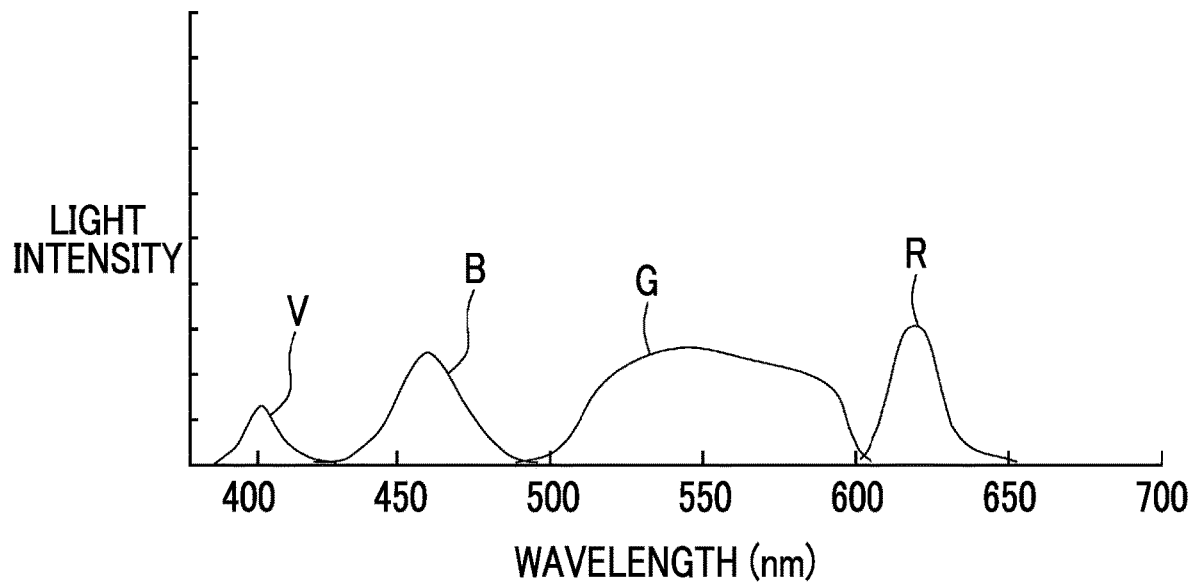
FIG. 3 is a graph showing the light emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source control unit 21 controls the V-LED 20a, the B-LED 20b, the G-LED 20c, and the R-LED 20d. Further, the light source control unit 21 controls the respective LEDs 20a to 20d so that normal light of which the light intensity ratios of violet light V, blue light B, green light G, and red light R are Vc:Bc:Gc:Rc is emitted in a normal light observation mode.

Further, in a case where a mode is set to the composite display mode, the light source control unit 21 performs control to emit each of first illumination light for illuminating the first object to be observed and second illumination light for illuminating the second object to be observed for a light emission period of one or more frames and to automatically switch and emit the first illumination light and the second illumination light. The first illumination light is emitted so that the light intensity ratios of violet light V, blue light B, green light G, and red light R are Vs1:Bs1:Gs1:Rs1.

Figure 4:
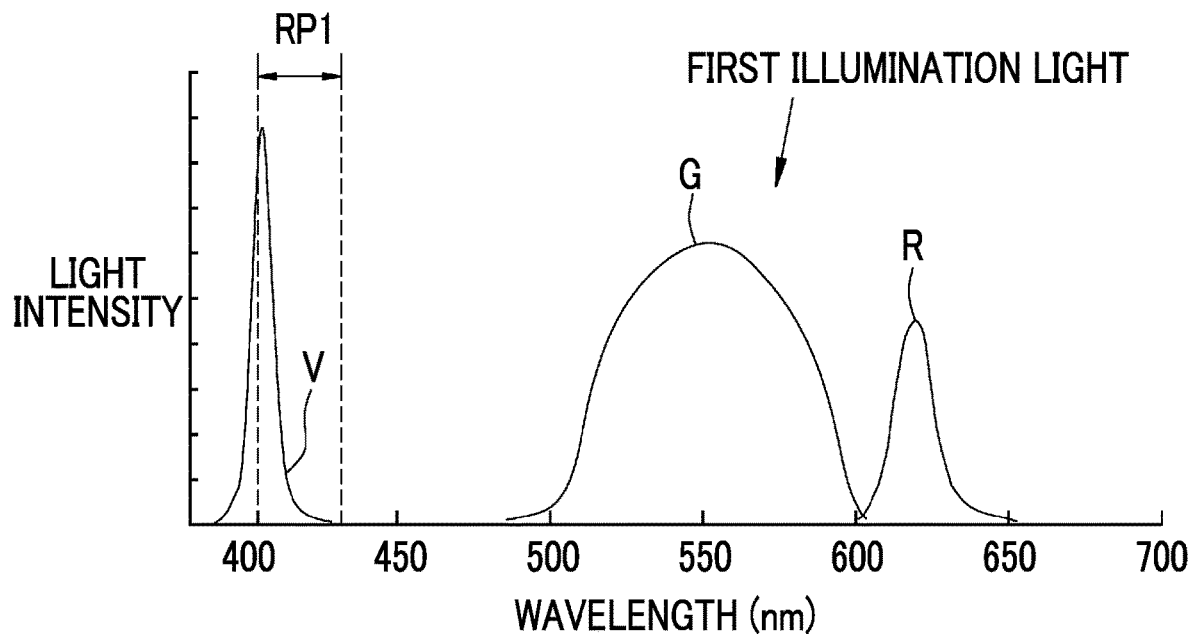
FIG. 4 is a graph showing the light emission spectrum of first illumination light that includes violet light V, green light G, and red light R.
Figure 5:
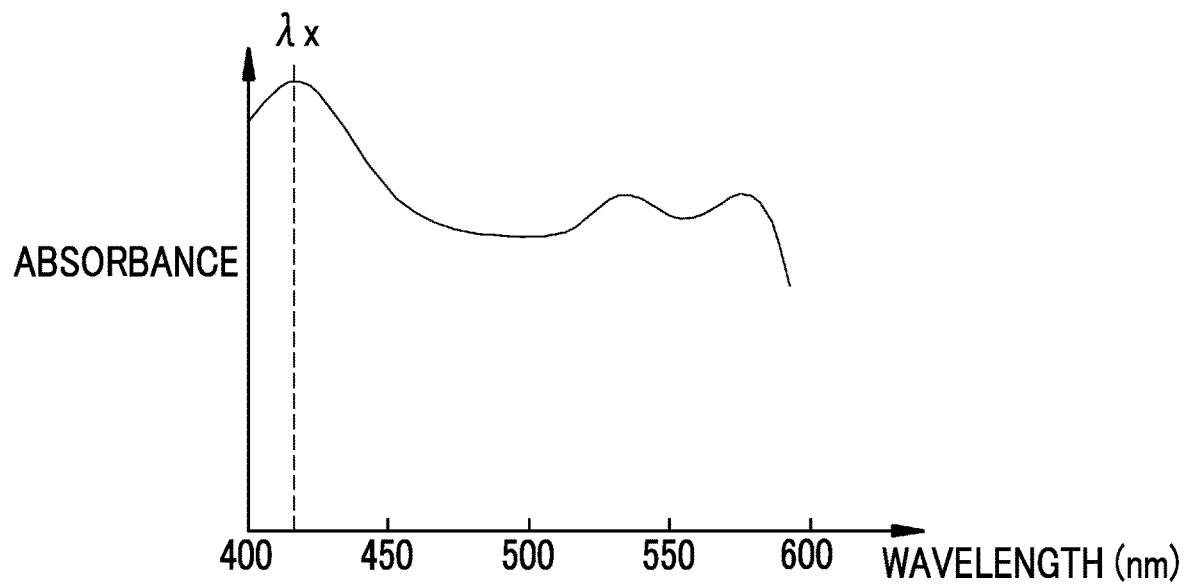
FIG. 5 is a graph showing the light absorption characteristics of hemoglobin.

It is preferable that violet light V of the first illumination light has a peak wavelength as shown in FIG. 4 for the emphasis of the first object to be observed, such as blood, in an image. In a case where violet light V has a peak wavelength as described above, a first absorption peak, such as an absorption peak Xx (see FIG. 5) of hemoglobin of blood or the like, is included in a first peak wavelength range RP1 of the first illumination light. Accordingly, the first object to be observed, such as blood, is emphasized by the first illumination light. Further, it is preferable that Bs1 of the first illumination light is set to "0" and Vs1, Gs1, and Rs1 of the first illumination light are set to be larger than 0. Here, it is preferable that the first peak wavelength range RP1 is in the range of 400 nm to 430 nm. Furthermore, it is preferable that the first absorption peak is included in a wavelength range including a wavelength of 410 nm or is about 410 nm. Hemoglobin has the absorption peak wavelength of light in a green-light wavelength range in addition to a blue-light wavelength range.

In this specification, the light intensity ratio includes a case where the ratio of at least one LED is zero. Accordingly, the light intensity ratio includes a case where one or two or more of the respective LEDs are not turned on. For example, it is assumed that light has light intensity ratios even in a case where only one LED is turned on and the other three LEDs are not turned on as in a case where the light intensity ratios of violet light V, blue light B, green light G, and red light R are 1:0:0:0.

Figure 6:
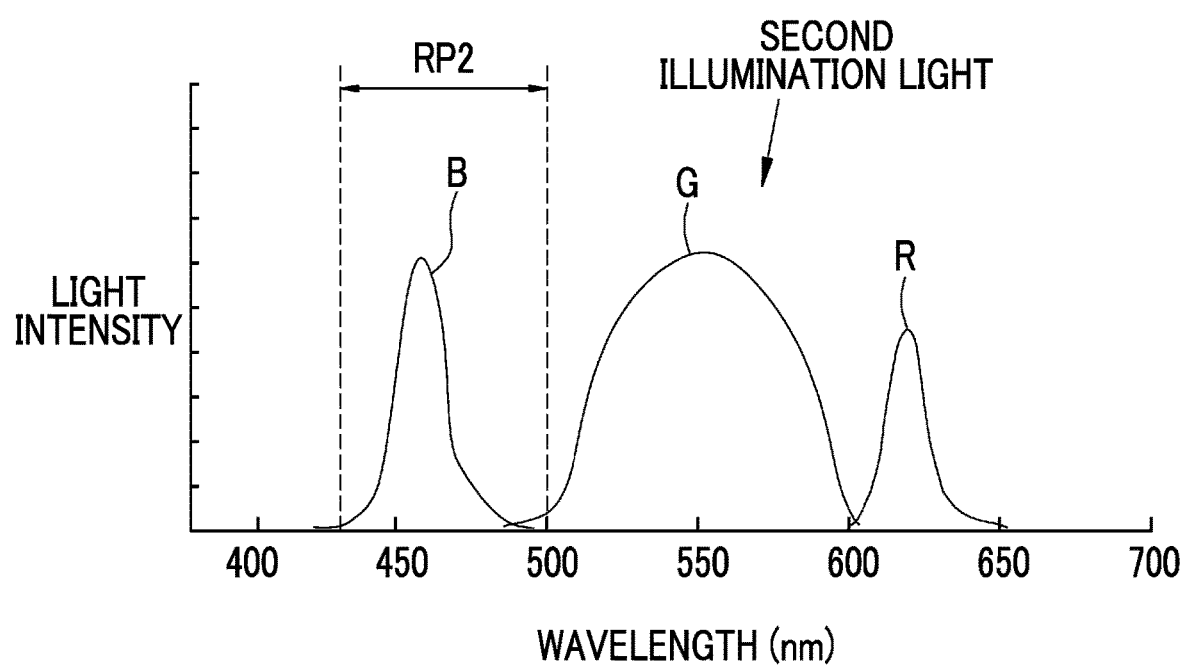
FIG. 6 is a graph showing the light emission spectrum of second illumination light that includes blue light B, green light G, and red light R.
Figure 7:
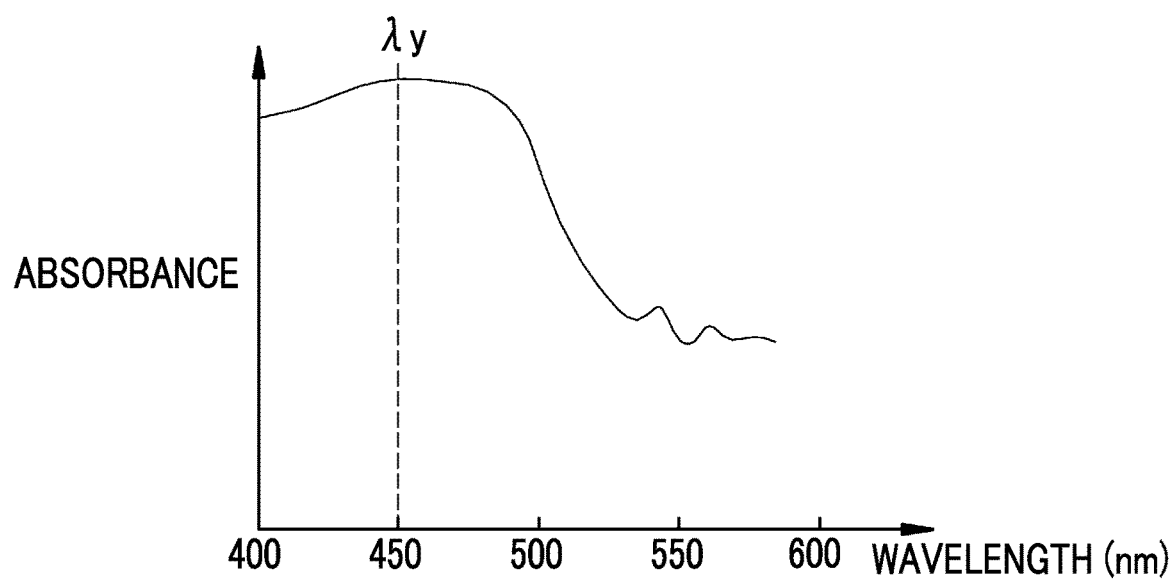
FIG. 7 is a graph showing the light absorption characteristics of a carcinoid.
Figure 8:
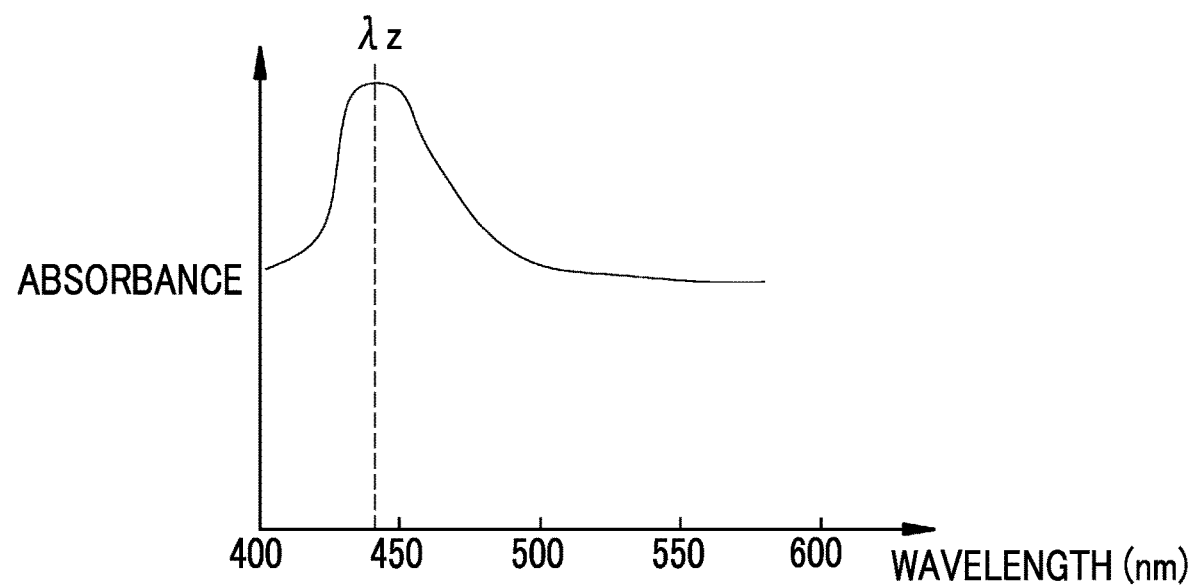
FIG. 8 is a graph showing the light absorption characteristics of bilirubin.

The second illumination light is emitted so that the light intensity ratios of violet light V, blue light B, green light G, and red light R are Vs2:Bs2:Gs2:Rs2. It is preferable that blue light B of the second illumination light has a peak wavelength as shown in FIG. 6 for the emphasis of the second object to be observed, such as bile or fat, in an image. In a case where blue light B has a peak wavelength as described above, a second absorption peak, such as an absorption peak λy (see FIG. 7) of a carcinoid included in fat and an absorption peak Xz (see FIG. 8) of bilirubin included in bile, is included in a second peak wavelength range RP2 of the second illumination light. Accordingly, the second object to be observed, such as bile or fat, is emphasized by the second illumination light. Further, it is preferable that Vs2 of the second illumination light is set to "0" and Bs1, Gs1, and Rs1 of the second illumination light are set to be larger than 0. Here, it is preferable that the second peak wavelength range RP2 is in the range of 430 nm to 500 nm. Furthermore, it is preferable that the second absorption peak is included in a wavelength range including a wavelength of 440 nm or 450 nm or is about 440 nm or about 450 nm.

Further, it is preferable that the light source control unit 21 sets the light intensity ratios (Gs1 and Rs1) of green light G and red light R included in the first illumination light and the light intensity ratios (Gs2 and Rs2) of green light G and red light R included in the second illumination light to the same light intensity ratios in the composite display mode. Accordingly, the tint of a background mucous membrane of a first display image obtained in a case where the first illumination light is applied is the same as that of a second display image obtained in a case where the second illumination light is applied. The background mucous membrane means a region of an object to be observed that does not include a region to be recognized or to be subjected to image pickup as a structure, such as a blood vessel or a glandular structure.

Figure 9:
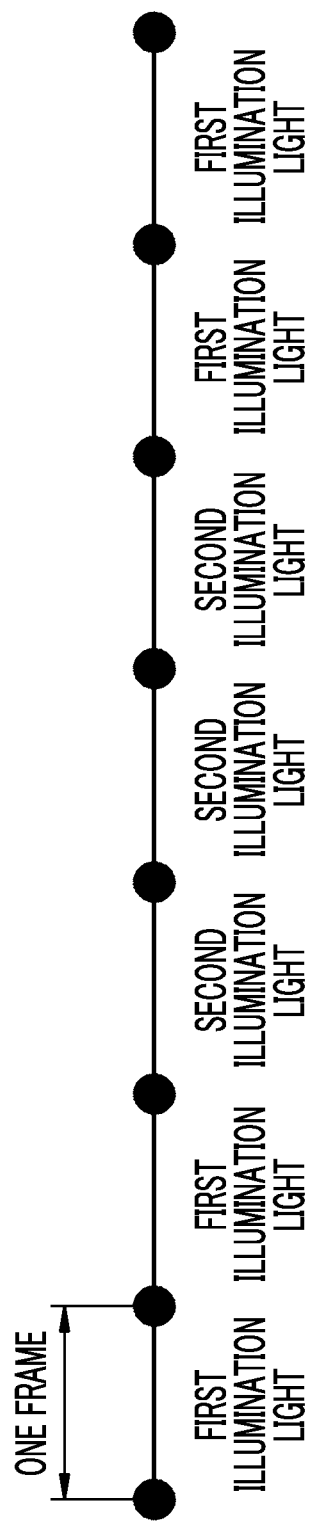
FIG. 9 is a diagram showing the light emission period of the first illumination light and the light emission period of the second illumination light.

Further, the light source control unit 21 controls the amount of illumination light, which is emitted from each of the LEDs 20*a* to 20*d*, on the basis of brightness information that is sent from a brightness information-calculation unit 54 of the processor device 16. Furthermore, in a case where the light source control unit 21 sets, for example, the light emission period of the first illumination light to two frames and sets the light emission period of the second illumination light to three frames, the second illumination light continues to be emitted for three frames after the first illumination light continues to be emitted for two frames as shown in FIG. 9.

"Frame" means a unit for the control of an image pickup sensor 48 that picks up an object to be observed. For example, "one frame" means a period including at least an exposure period where the image pickup sensor 48 is exposed to light emitted from an object to be observed and a reading period where an image signal is read out. In this embodiment, a light emission period is determined so as to correspond to "frame" that is the unit of image pickup.

Figure 10:
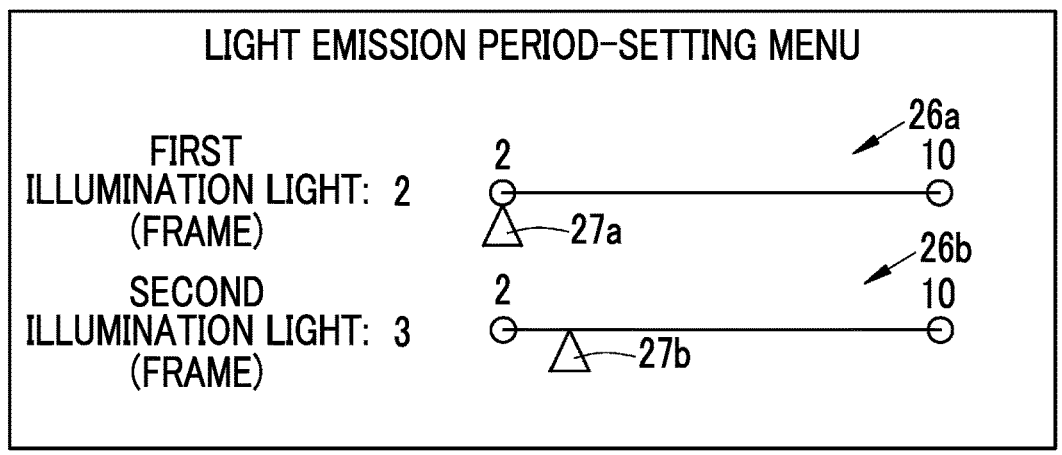
FIG. 10 is a diagram showing a light emission period-setting menu.

The light emission period of the first illumination light and the light emission period of the second illumination light can be appropriately changed by a light emission period-setting unit 24 that is connected to the light source control unit 21. In a case where an operation for changing a light emission period is received by the operation of the user interface 19, the light emission period-setting unit 24 displays a light emission period-setting menu shown in FIG. 10 on the monitor 18. The light emission period of the first illumination light can be changed between, for example, two frames and ten frames. Each light emission period is assigned to a slide bar 26*a*.

In a case where the light emission period of the first illumination light is to be changed, a user operates the user interface 19 to position a slider 27*a* at a position on the slide bar 26*a* that represents a light emission period to which the user wants to change a light emission period. Accordingly, the light emission period of the first illumination light is changed. Even in the case of the light emission period of the second illumination light, a user operates the user interface 19 to position a slider 27*b* at a position on a slide bar 26*b* (to which a light emission period in the range of two frames to ten frames is assigned) that represents a light emission period to which the user wants to change a light emission period. Accordingly, the light emission period of the second illumination light is changed.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12*d* of the endoscope 12. A multimode fiber can be used as the light guide 41. For example, a thin fiber cable of which a total diameter of a core diameter of 105 μm, a cladding diameter of 125 μm, and a protective layer forming a covering is in the range of φ0.3 to 0.5 mm can be used.

The distal end part 12*d* of the endoscope 12 is provided with an illumination optical system 30*a* and an image pickup optical system 30*b*. The illumination optical system 30*a* includes an illumination lens 45, and light transmitted from the light guide 41 is applied to an object to be observed through the illumination lens 45. The image pickup optical system 30*b* includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels (specific pixels) provided with B-filters. Since the B-pixels transmit light in a wavelength range, which corresponds to the first peak wavelength range of the first illumination light and the peak wavelength range of the second illumination light, in the composite display mode, both components of the first object to be observed and components of the second object to be observed are included in signals output from the B-pixels.

Image signals for normal light are obtained in a case where the image of an object to be observed illuminated with normal light is picked up by the image pickup sensor 48. The image signals for normal light include blue signals for normal light that are output from the B-pixels, green signals for normal light that are output from the G-pixels, and red signals for normal light that are output from the R-pixels. First image signals are obtained in a case where the image of an object to be observed illuminated with the first illumination light is picked up by the image pickup sensor 48. The first image signals include first blue signals B1 that are output from the B-pixels, first green signals G1 that are output from the G-pixels, and first red signals R1 that are output from the R-pixels. Second image signals are obtained in a case where the image of an object to be observed illuminated with the second illumination light is picked up by the image pickup sensor 48. The second image signals include second blue signals B2 that are output from the B-pixels, second green signals G2 that are output from the G-pixels, and second red signals R2 that are output from the R-pixels.

Figure 11:
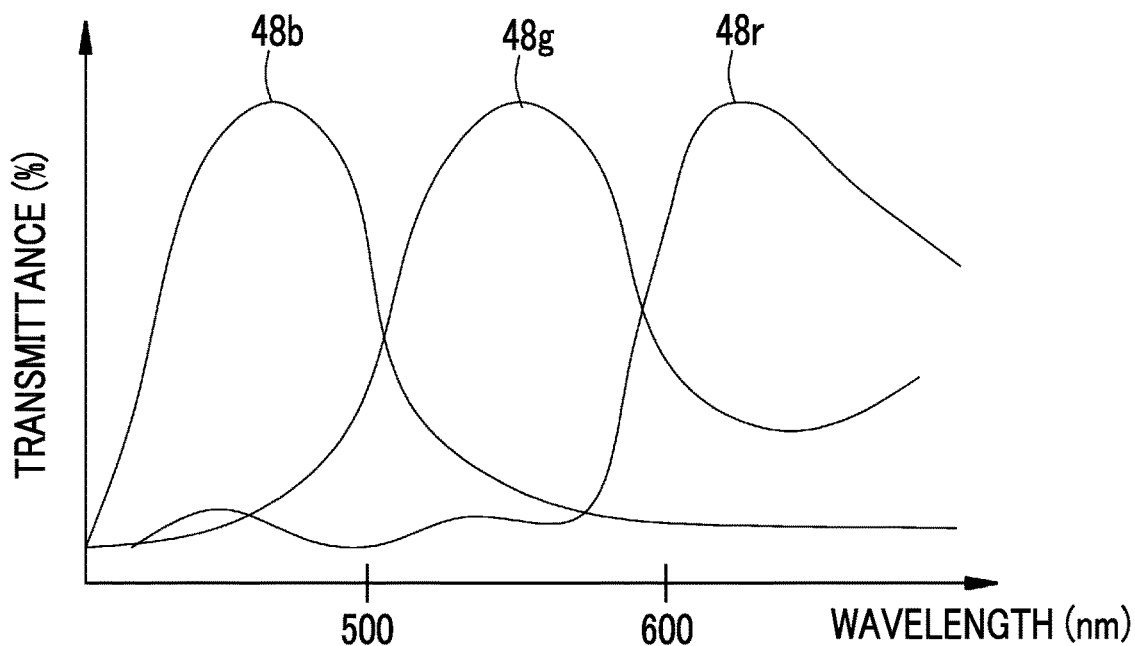
FIG. 11 is a graph showing the spectral transmission characteristics of a B-filter, a G-filter, and an R-filter provided on an image pickup sensor.

As shown in FIG. 11, the B-filter 48*b* transmits light in a violet-light wavelength range, light in a blue-light wavelength range, and short-wavelength light of light in a green-light wavelength range. The G-filter 48*g* transmits light in a green-light wavelength range, long-wavelength light of light in a blue-light wavelength range, and short-wavelength light of light in a red-light wavelength range. The R-filter 48*r* transmits light in a red-light wavelength range and short-wavelength light of light in a green-light wavelength range. Accordingly, the B-pixel of the image pickup sensor 48 is sensitive to violet light V, blue light B, and green light G; the G-pixel thereof is sensitive to blue light B, green light G, and red light R; and the R-pixel is sensitive to green light G and red light R.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of CMYG are output. Accordingly, the image signals corresponding to four colors of CMYG need to be converted into image signals corresponding to three colors of RGB by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

As shown in FIG. 2, the image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 comprises an image acquisition unit 53, a brightness information-calculation unit 54, a digital signal processor (DSP) 56, a noise removing unit 58, a signal switching unit 60, a normal observation image-processing unit 62, a composite display image-processing unit 63, a display control unit 66, a static image storage unit 67, and a static image-storage-control unit 68.

The image acquisition unit 53 acquires an observation image that is obtained in a case where the image of an object to be observed is picked up by the endoscope 12. Specifically, digital color image signals output from the endoscope 12 are input to the image acquisition unit 53 as the observation image. The color image signals are formed of red signals that are output from the R-pixels of the image pickup sensor 48, green signals that are output from the G-pixels of the image pickup sensor 48, and blue signals that are output from the B-pixels of the image pickup sensor 48. The brightness information-calculation unit 54 calculates brightness information, which represents the brightness of the object to be observed, on the basis of the image signals that are input from the image acquisition unit 53. The calculated brightness information is sent to the light source control unit 21, and is used for the control of the amount of emitted illumination light.

The DSP 56 performs various kinds of signal processing, such as defect correction processing, offset processing, gain correction processing, linear matrix processing, gamma conversion processing, and demosaicing processing, on the received image signals. Signals of defective pixels of the image pickup sensor 48 are corrected in the defect correction processing. Dark current components are removed from the image signals subjected to the defect correction processing in the offset processing, so that an accurate zero level is set. The image signals subjected to the offset processing are multiplied by a specific gain in the gain correction processing, so that signal levels are adjusted. Linear matrix processing for improving color reproducibility is performed on the image signals subjected to the gain correction processing. After that, brightness or a saturation is adjusted by the gamma conversion processing. The demosaicing processing (also referred to as equalization processing or demosaicing) is performed on the image signals subjected to the linear matrix processing, so that signals of colors deficient in each pixel are generated by interpolation. All the pixels are made to have the signals of the respective colors by this demosaicing processing.

The noise removing unit 58 performs noise removal processing (for example, a moving-average method, median filtering, or the like) on the image signals, which have been subjected to gamma correction and the like by the DSP 56, to remove noise from the image signals. The image signals from which noise has been removed are transmitted to the signal switching unit 60.

In a case where a mode is set to the normal light observation mode by the mode changeover switch 13*a*, the signal switching unit 60 transmits the image signals for normal light obtained from illumination using normal light and image pickup to the normal observation image-processing unit 62. In a case where a mode is set to the composite display mode, the signal switching unit 60 transmits the first image signals obtained from illumination using the first illumination light and image pickup and the second image signals obtained from illumination using the second illumination light and image pickup to the composite display image-processing unit 63.

The normal observation image-processing unit 62 performs image processing for a normal image on the image signals for normal light. The image processing for a normal image includes structure emphasis processing for a normal image and the like. The normal observation image-processing unit 62 is provided with a parameter for a normal image which is to be multiplied by normal image signals to perform the image processing for a normal image. RGB image signals subjected to the image processing for a normal image are input to the display control unit 66 from the normal observation image-processing unit 62 as a normal image.

The composite display image-processing unit 63 synthesizes the first image signals and the second image signals to generate a composite display image of one frame. The first object to be observed, such as blood, and the second object to be observed, such as bile or fat, are displayed in the composite display image to be identifiable. The details of a method of generating the composite display image will be described later. The generated composite display image is input to the display control unit 66 from the composite display image-processing unit 63.

The display control unit 66 performs control to display the normal image or the composite display image, which is input from the normal observation image-processing unit 62 or the composite display image-processing unit 63, as an image that can be displayed by the monitor 18. An image corresponding to each observation mode is displayed by the control that is performed by the display control unit 66. The normal image is displayed on the monitor 18 in the normal light observation mode. Further, the composite display image is displayed on the monitor 18 in the composite display mode.

The static image-storage-control unit 68 performs control to store an image, which is obtained at the timing of a static image-acquisition instruction, in the static image storage unit 67 as a static image according to the instruction of the static image-acquisition instruction unit 13*b*. In the normal light observation mode, the static image-storage-control unit 68 stores a normal image, which is obtained at the timing of a static image-acquisition instruction, in the static image storage unit 67 as a static image. In the composite display mode, the static image-storage-control unit 68 stores a composite display image, which is obtained at the timing of a static image-acquisition instruction, in the static image storage unit 67 as a static image.

Next, the details of a method of generating the composite display image and the like will be described. The composite display image-processing unit 63 performs identification processing for displaying the first object to be observed and the second object to be observed in a composite display image to allow the first object to be observed and the second object to be observed to be identified. The identification processing includes first identification processing for comparing the signal value of a specific color signal of the first image signals with the signal value of a specific color signal of the second image signals by comparison processing and displaying the first object to be observed and the second object to be observed in the composite display image to allow the first object to be observed and the second object to be observed to be identified by using the result of the comparison processing.

Figure 12:
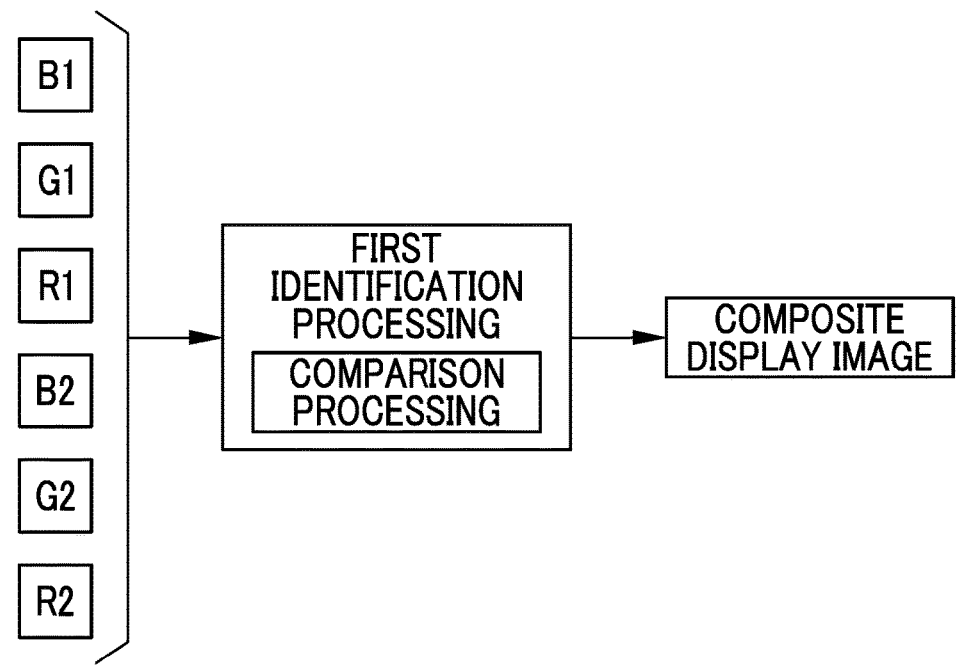
FIG. 12 is a diagram showing first identification processing.

Specifically, as shown in FIG. 12, a composite display image is generated in the first identification processing on the basis of a first blue signal B1, a first green signal G1, a first red signal R1, a second blue signal B2, a second green signal G2, and a second red signal R2. Here, since many components related to the first absorption peak of blood that is the first object to be observed are included in the reflected light component of violet light V, the components related to the first absorption peak are included in the first blue signal B1 (specific color signal) of the first image signals. Further, since many components related to the second absorption peak of bile or fat that is the second object to be observed are included in the reflected light component of blue light B, the components related to the first absorption peak are included in the second blue signal B2 (specific color signal) of the second image signals.

Figure 13:
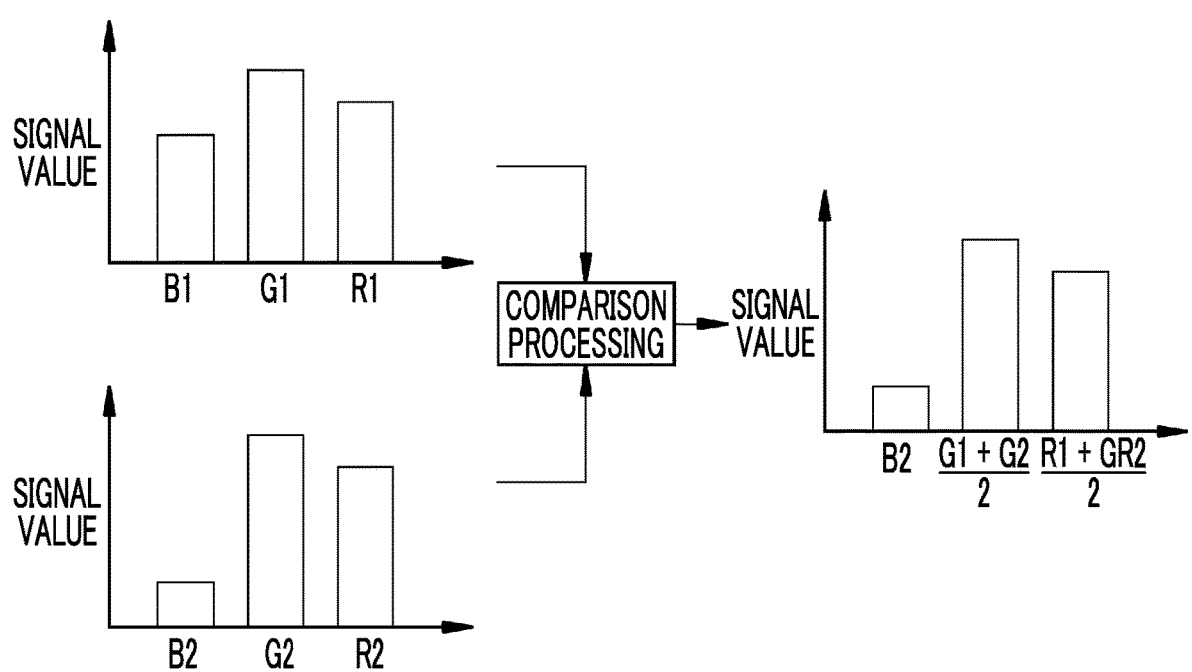
FIG. 13 is a diagram showing comparison processing.

For this reason, in a case where the image of the first object to be observed is picked up, the signal value of the first blue signal B1 is smaller than the signal value of the second blue signal B2. In contrast, in a case where the image of the second object to be observed is picked up, the signal value of the second blue signal B2 is smaller than the signal value of the first blue signal B1. As shown in FIG. 13, the signal value of the first blue signal B1 and the signal value of the second blue signal B2 are compared with each other as comparison processing by using the above-mentioned relationship. Then, as the result of the comparison processing, a signal having a smaller signal value is displayed in the composite display image as the B-image of the composite display image and a signal having a larger signal value is not displayed in the composite display image. Accordingly, the first object to be observed and the second object to be observed can be selectively displayed in one composite display image. That is, the first object to be observed and the second object to be observed can be identified and displayed in the composite display image.

Since a ratio of the amount of green light to the amount of red light in the first illumination light is set to be substantially equal to that in the second illumination light, the signal value of the first green signal G1 and the signal value of the second green signal G2 are substantially equal to each other and the signal value of the first red signal R1 and the signal value of the second red signal R2 are also substantially equal to each other. The colors of the image of a color chart in a case where the color chart (for example, macbeth) is illuminated with the first illumination light and the image of the color chart is picked up are substantially the same as those in a case where the color chart is illuminated with the second illumination light and the image of the color chart is picked up (a premise is to adjust not only the amount of illumination light but also white balance). Accordingly, it is preferable that the G-image of the composite display image is displayed by an average value of the signal value of the first green signal G1 and the signal value of the second green signal G2. Further, it is preferable that the R-image of the composite display image is displayed by an average value of the signal value of the first red signal R1 and the signal value of the second red signal R2.

Furthermore, a signal having a smaller signal value between the first blue signal B1 and the second blue signal B2 is displayed in the composite display image as the B-image of the composite display image and a signal having a larger signal value therebetween is not displayed in the composite display image in the first identification processing, so that both the first object to be observed (for example, blood) and the second object to be observed (for example, bile or fat) are emphasized. However, other processing may be performed. For example, the first blue signal B1 may be displayed as the B-image of the composite display image and the second blue signal B2 may not be displayed, so that only the first object to be observed is emphasized. Further, the second blue signal B2 may be displayed as the B-image of the composite display image and the first blue signal B1 may not be displayed, so that only the second object to be observed is emphasized. Furthermore, a signal having a larger signal value between the first blue signal B1 and the second blue signal B2 is displayed in the composite display image as the B-image of the composite display image and a signal having a smaller signal value therebetween is not displayed in the composite display image, so that the display of both the first object to be observed (for example, blood) and the second object to be observed (for example, bile or fat) is suppressed (for example, both the first object to be observed and the second object to be observed are not easily seen).

Figure 14:
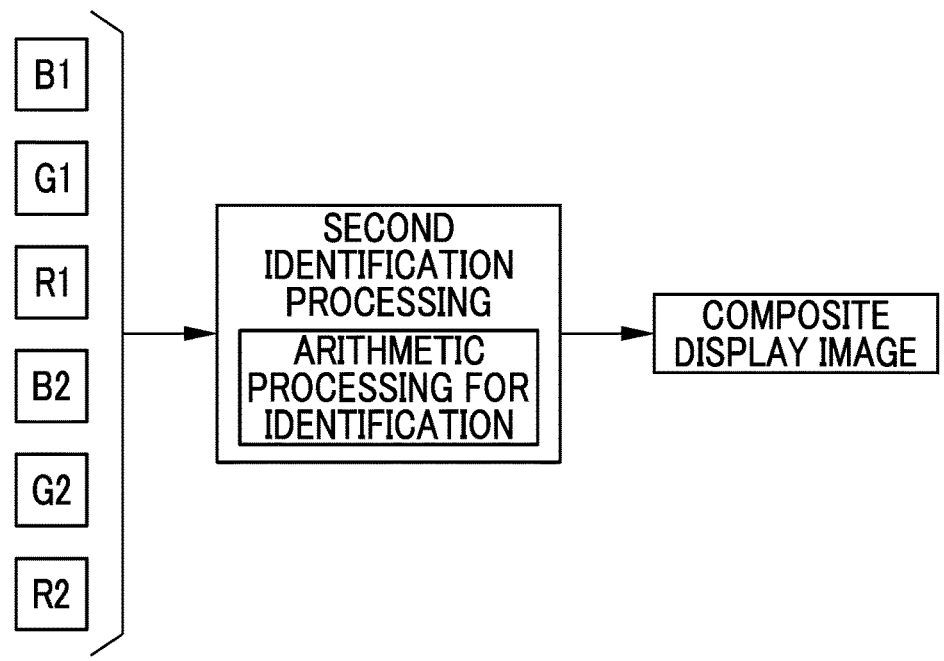
FIG. 14 is a diagram showing second identification processing.

Moreover, the identification processing includes second identification processing for performing arithmetic processing for identification based on a specific color signal of the first image signals and a specific color signal of the second image signals and displaying the first object to be observed and the second object to be observed in the composite display image to allow the first object to be observed and the second object to be observed to be identified by using the result of the arithmetic processing for identification. Specifically, as shown in FIG. 14, a composite display image is generated in the first identification processing on the basis of a first blue signal B1, a first green signal G1, a first red signal R1, a second blue signal B2, a second green signal G2, and a second red signal R2.

Figure 15:
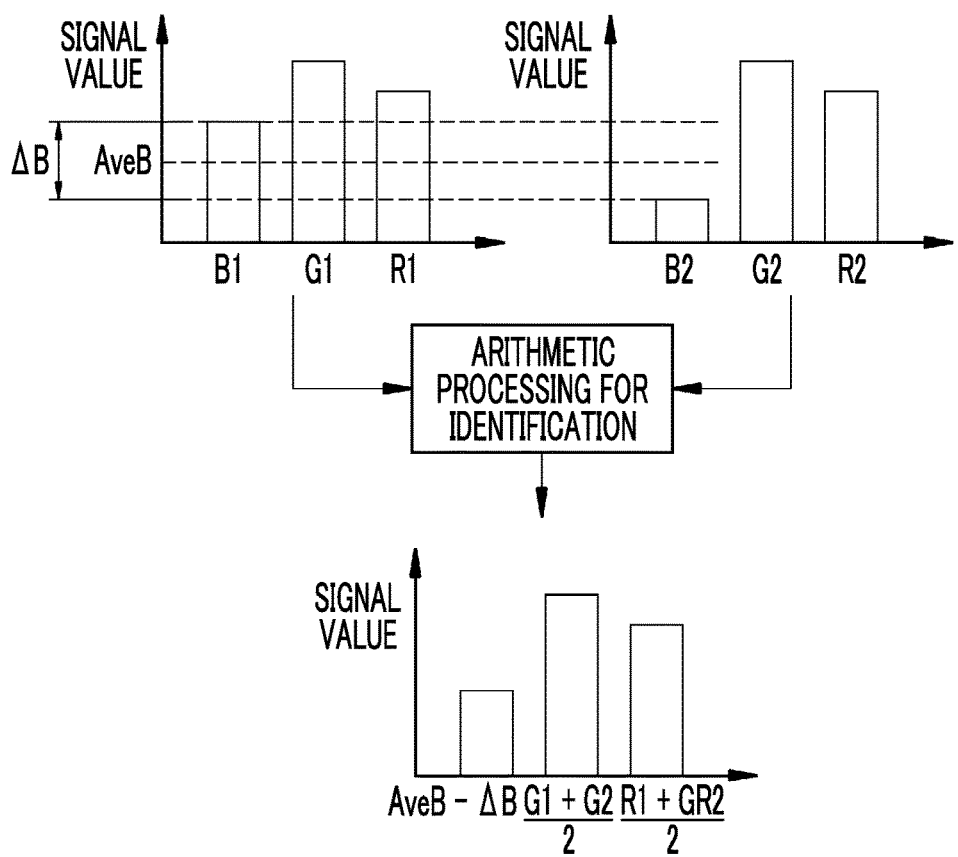
FIG. 15 is a diagram showing arithmetic processing for identification.

Then, an arithmetic processing for identification is performed using the fact that a relationship between the signal value of the first blue signal B1 and the signal value of the second blue signal B2 is changed as described above in a case where the image of the first object to be observed is picked up and a case where the image of the second object to be observed is picked up. In the arithmetic processing for identification, as shown in FIG. 15, an average value AveB of the signal value of the first blue signal B1 and the signal value of the second blue signal B2 is obtained and an absolute value ΔB of a difference value between the signal value of the first blue signal B1 and the signal value of the second blue signal B2 is obtained. Then, the B-image of the composite display image is displayed according to an arithmetic value that is obtained by subtracting ΔB from AveB. Accordingly, the first object to be observed and the second object to be observed can be selectively displayed in one composite display image. That is, the first object to be observed and the second object to be observed can be identified and displayed in the composite display image. In addition, since the arithmetic value is smaller than the signal value of the first blue signal B1 or the signal value of the second blue signal B2, the first object to be observed and the second object to be observed are more clearly distinguished from each other and displayed.

Figure 16:
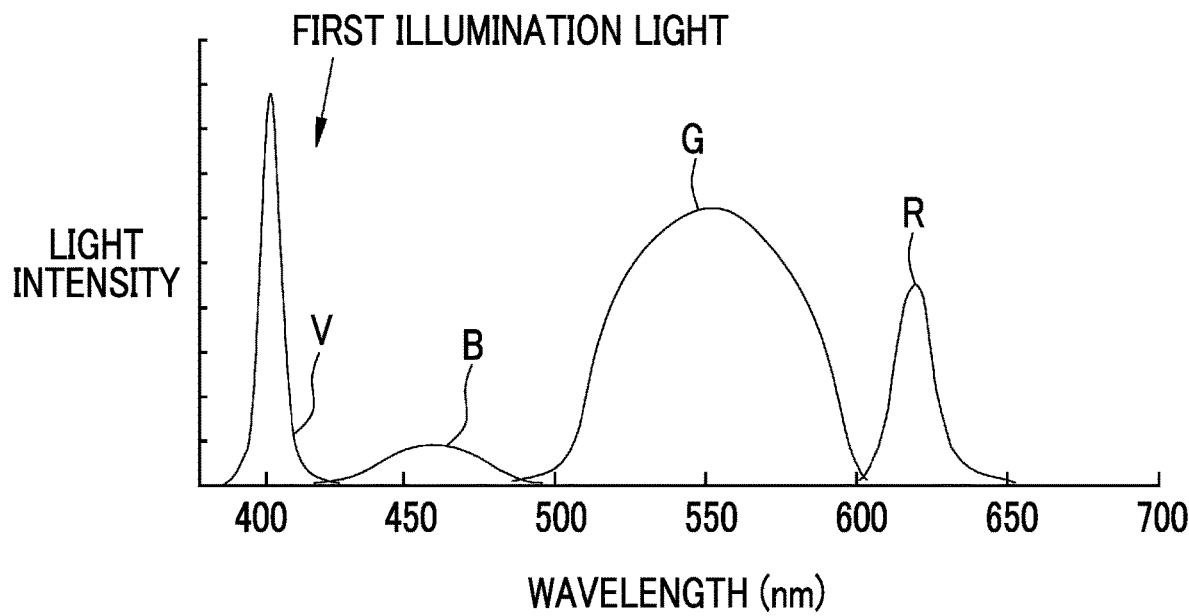
FIG. 16 is a graph showing the light emission spectrum of first illumination light which includes violet light V, blue light B, green light G, and red light R and of which the light intensity of the violet light V is higher than the light intensity of the blue light B.

The first illumination light includes violet light V, green light G, and red light R in the above-mentioned embodiment, but blue light B may be added to the first illumination light as shown in FIG. 16 so that the first illumination light includes violet light V, blue light B, green light G, and red light R. In this case, the light intensity of violet light V is set to be higher than the light intensity of blue light B. For example, it is preferable that the ratios of the light intensity Vs1 of violet light V and the light intensity Bs1 of blue light B are set to "9:1".

Figure 17:
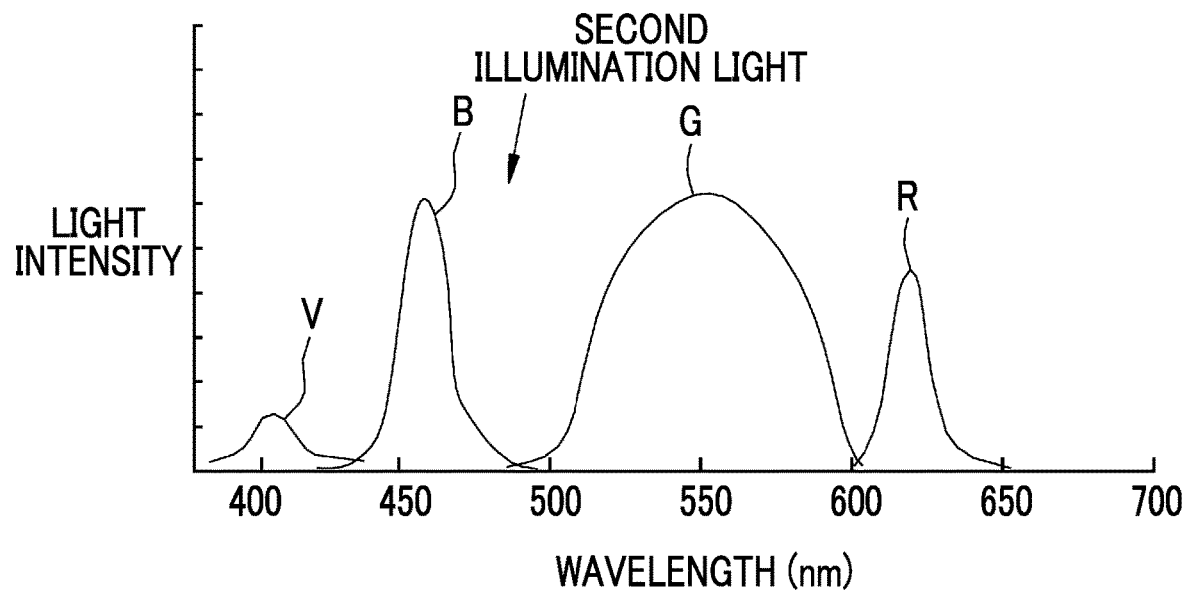
FIG. 17 is a graph showing the light emission spectrum of second illumination light which includes violet light V, blue light B, green light G, and red light R and of which the light intensity of the blue light B is higher than the light intensity of the violet light V.

Further, the second illumination light includes blue light B, green light G, and red light R, but violet light V may be added to the second illumination light as shown in FIG. 17 so that the second illumination light includes violet light V, blue light B, green light G, and red light R. In this case, the light intensity of blue light B is set to be higher than the light intensity of violet light V. For example, it is preferable that the ratios of the light intensity Vs2 of violet light V and the light intensity Bs2 of blue light B are set to "1:9". In a case where each of the first illumination light and the second illumination light includes violet light V, blue light B, green light G, and red light R as described above, it is preferable that the intensity ratio of violet light included in the first illumination light and the intensity ratio of violet light included in the second illumination light are set to be different from each other and the intensity ratio of blue light included in the first illumination light and the intensity ratio of blue light included in the second illumination light are set to be different from each other in a state where the light intensity ratios of green light and red light included in the first illumination light and the light intensity ratios of green light and red light included in the second illumination light are set to be substantially equal to each other.

Second Embodiment

Figure 18:
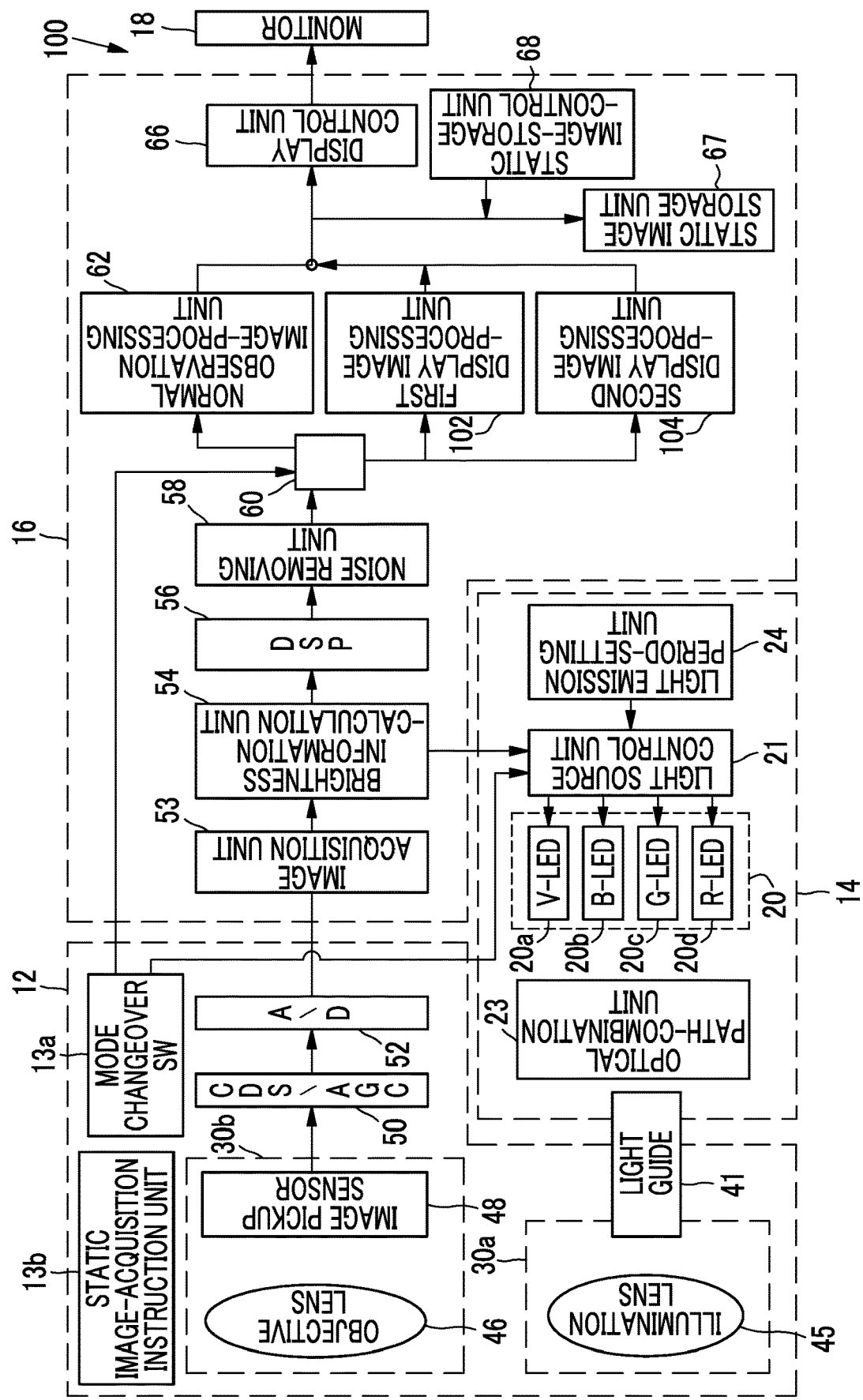
FIG. 18 is a block diagram showing the functions of an endoscope system according to a second embodiment.

In the first embodiment, the first object to be observed and the second object to be observed are identified and displayed in one composite display image. However, in a second embodiment, a first object to be observed and a second object to be observed are displayed to be identifiable by the switching and display of a plurality of display images. As shown in FIG. 18, a first display image-processing unit 102 and a second display image-processing unit 104 are provided in an endoscope system 100 according to the second embodiment instead of the composite display image-processing unit 63. Others of the endoscope system 100 are the same as those of the endoscope system 10 according to the first embodiment.

A multi-observation mode is provided in the endoscope system 100 according to the second embodiment instead of the composite display mode of the first embodiment. In a case where a mode is set to the multi-observation mode in the endoscope system 100, first image signals obtained from illumination using first illumination light and image pickup are transmitted to the first display image-processing unit 102 and second image signals obtained from illumination using second illumination light and image pickup are transmitted to the second display image-processing unit 104. The first display image-processing unit 102 performs image processing for a first display image on the first image signals and outputs the first image signals. The second display image-processing unit 104 performs image processing for a second display image on the second image signals and outputs the second image signals.

Figure 19:
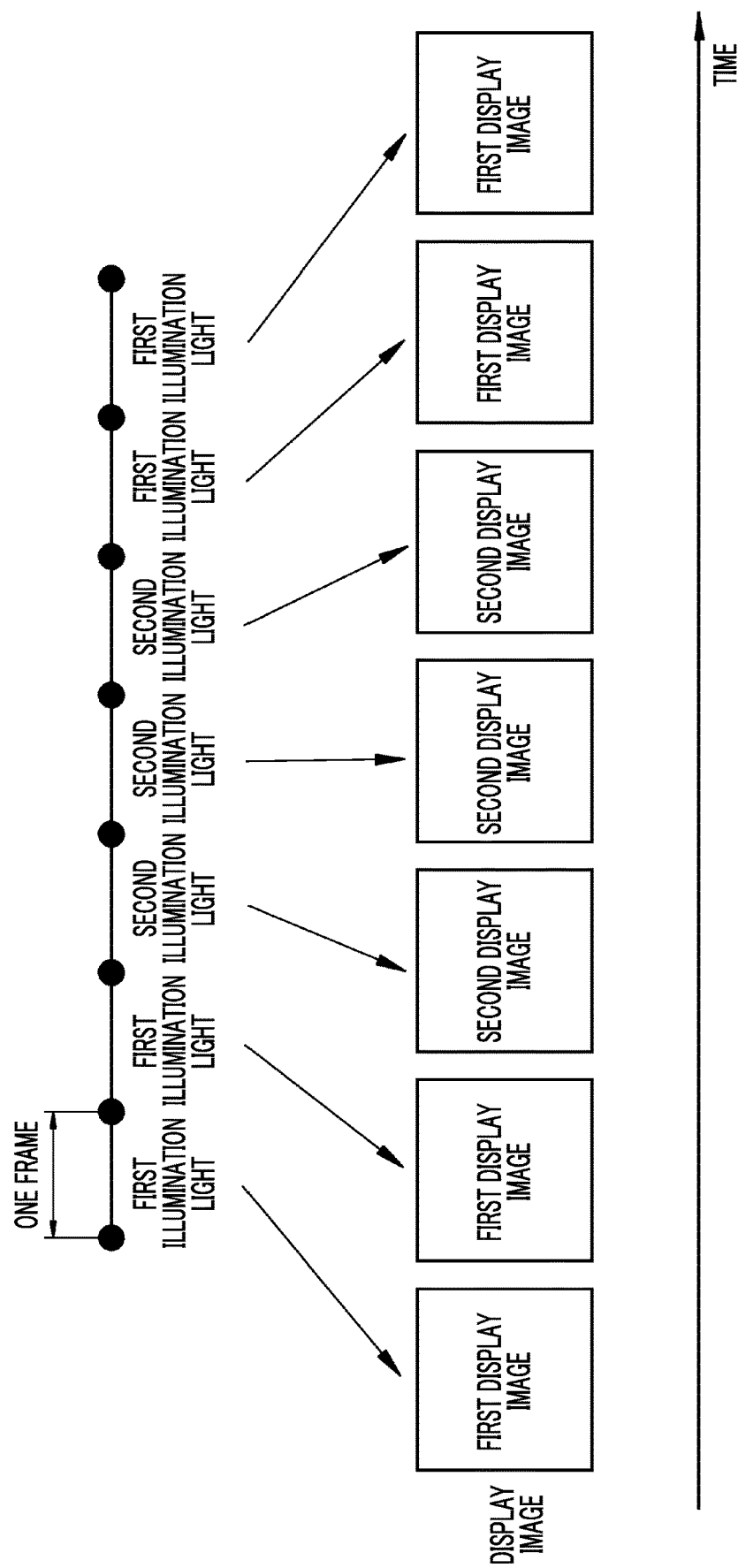
FIG. 19 is a diagram showing the switching display of first and second display images.

Then, in the multi-observation mode, the display control unit 66 switches the first display image and second display image according to the light emission period of the first illumination light and the light emission period of the second illumination light and displays one of the first display image and second display image on the monitor 18. That is, in a case where the light emission period of the first illumination light is two frames and the light emission period of the second illumination light is three frames, the first display image continues to be displayed for two frames and the second display image continues to be displayed for three frames as shown in FIG. 19. Accordingly, since the first object to be observed, such as blood, and the second object to be observed, such as bile or fat, are alternately displayed on the monitor 18, the first object to be observed and the second object to be observed are displayed to be identifiable.

The hardware structures of the processing units, which are included in the processor device 16 in the first and second embodiments, such as the image acquisition unit 53, the brightness information-calculation unit 54, the DSP 56, the noise removing unit 58, the normal observation image-processing unit 62, the composite display image-processing unit 63, the static image storage unit 67, the display control unit 66, the static image-storage-control unit 68, the first display image-processing unit 102, and the second display image-processing unit 104, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a graphical processing unit (GPU); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, a combination of a CPU and an FPGA, or a combination of a CPU and a GPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

The invention can be applied to various medical image processing devices other than the processor device that is to be combined with the endoscope systems described in the first and second embodiments.

EXPLANATION OF REFERENCES

10: endoscope system
12: endoscope
12*a*: insertion part
12*b*: operation part 12c: bendable part
12d: distal end part
12e: angle knob
13a: mode changeover switch
13b: static image-acquisition instruction unit
14: light source device
16: processor device
18: monitor
19: user interface
20: light source unit
20a: V-LED (violet light emitting diode)
20b: B-LED (blue light emitting diode)
20c: G-LED (green light emitting diode)
20d: R-LED (red light emitting diode)
21: light source control unit
23: optical path-combination unit
24: light emission period-setting unit
26a: slide bar
26b: slide bar
27a: slider
27b: slider
30a: illumination optical system
30b: image pickup optical system
41: light guide
45: illumination lens
46: objective lens
48: image pickup sensor
48b: B-filter
48g: G-filter
48r: R-filter
50: CDS/AGC circuit
53: image acquisition unit
54: brightness information-calculation unit
56: DSP (digital signal processor)
58: noise removing unit
60: signal switching unit
62: normal observation image-processing unit
63: composite display image-processing unit
66: display control unit
67: static image storage unit
68: static image-storage-control unit
100: endoscope system
102: first display image-processing unit
104: second display image-processing unit
RP1: first peak wavelength range
RP2: second peak wavelength range
λx: absorption peak of hemoglobin
λy: absorption peak of carcinoid
λz: absorption peak of bilirubin

What is claimed is:

1. An endoscope system comprising:
a light source unit that emits first illumination light having a first peak wavelength range and second illumination light having a second peak wavelength range different from the first peak wavelength range;
a light source control unit that automatically switches and emits the first illumination light and the second illumination light for a light emission period of at least one or more frames;
a color image pickup sensor that includes specific pixels provided with specific color filters transmitting light having a wavelength range corresponding to the first peak wavelength range and light having a wavelength range corresponding to the second peak wavelength range;
an image acquisition unit that acquires first image signals obtained in a case where an image of an object to be observed illuminated with the first illumination light is picked up by the image pickup sensor and second image signals obtained in a case where an image of an object to be observed illuminated with the second illumination light is picked up by the image pickup sensor; and
a composite display image-processing unit that performs identification processing for allowing a first object to be observed and a second object to be observed to be identified in a composite display image in a case where the composite display image-processing unit synthesizes the first image signals and the second image signals to generate the composite display image, the first object to be observed having a first absorption peak in the first peak wavelength range of the first illumination light and the second object to be observed having a second absorption peak in the second peak wavelength range of the second illumination light.

2. The endoscope system according to claim 1, wherein a component related to the first absorption peak of the first object to be observed is included in a specific color signal of the first image signal output from the specific pixel among the first image signals, and a component related to the second absorption peak of the second object to be observed is included in a specific color signal of the second image signal output from the specific pixel among the second image signals, and
the identification processing includes first identification processing for comparing a signal value of the specific color signal of the first image signal with a signal value of the specific color signal of the second image signal by comparison processing and displaying the first object to be observed and the second object to be observed to allow the first object to be observed and the second object to be observed to be identified in the composite display image by using a result of the comparison processing.

3. The endoscope system according to claim 2, wherein the specific color signal of the first image signal is displayed in the composite display image in the first identification processing.

4. The endoscope system according to claim 2, wherein the specific color signal of the second image signal is displayed in the composite display image in the first identification processing.

5. The endoscope system according to claim 2, wherein a signal having a smaller signal value between the specific color signal of the first image signal and the specific color signal of the second image signal is displayed in the composite display image and a signal having a larger signal value therebetween is not displayed in the composite display image in the first identification processing.

6. The endoscope system according to claim 2, wherein a signal having a larger signal value between the specific color signal of the first image signal and the specific color signal of the second image signal is displayed in the composite display image and a signal having a smaller signal value therebetween is not displayed in the composite display image in the first identification processing.

7. The endoscope system according to claim 1, wherein a component related to the first absorption peak of the first object to be observed is included in a specific color signal of the first image signal output from the specific pixel among the first image signals, and a component related to the second absorption peak of the second object to be observed is included in a specific color signal of the second image signal output from the specific pixel among the second image signals, and the identification processing includes second identification processing for performing arithmetic processing for identification based on the specific color signal of the first image signal and the specific color signal of the second image signal and displaying the first object to be observed and the second object to be observed to allow the first object to be observed and the second object to be observed to be identified in the composite display image by using a result of the arithmetic processing for identification.

8. The endoscope system according to claim 1, wherein the specific pixel is a B-pixel that is provided with a B-filter as the specific color filter.

9. The endoscope system according to claim 1, wherein the first peak wavelength range is in a range of 400 nm to 430 nm, and the second peak wavelength range is in a range of 430 nm to 500 nm.

10. The endoscope system according to claim 1, wherein the first absorption peak is included in a wavelength range including a wavelength of 410 nm and the second absorption peak is included in a wavelength range including a wavelength of 440 nm or 450 nm.

11. The endoscope system according to claim 1, wherein the first object to be observed is blood and the second object to be observed is bile or fat.

12. An endoscope system comprising:

a light source unit that emits first illumination light having a first peak wavelength range and second illumination light having a second peak wavelength range different from the first peak wavelength range;

a light source control unit that automatically switches and emits the first illumination light and the second illumination light for a light emission period of at least one or more frames;

a color image pickup sensor that includes specific pixels provided with specific color filters transmitting light having a wavelength range corresponding to the first peak wavelength range and light having a wavelength range corresponding to the second peak wavelength range;

an image acquisition unit that acquires first image signals obtained in a case where an image of an object to be observed illuminated with the first illumination light is picked up by the image pickup sensor and second image signals obtained in a case where an image of an object to be observed illuminated with the second illumination light is picked up by the image pickup sensor; and a display control unit that alternately displays a first display image based on the first image signals and a second display image based on the second image signals at regular intervals by a display unit to display a first object to be observed and a second object to be observed by the display unit and to allow the first object to be observed and the second object to be observed to be identified, the first object to be observed having a first absorption peak in the first peak wavelength range of the first illumination light and the second object to be observed having a second absorption peak in the second peak wavelength range of the second illumination light.

* * * * *